United States Patent [19]

Lerman

[11] Patent Number: 4,628,913

[45] Date of Patent: * Dec. 16, 1986

[54] CERVICAL THORACIC ORTHOSIS

[75] Inventor: Max Lerman, Beverly Hills, Calif.

[73] Assignee: United States Manufacturing Co., Pasadena, Calif.

[*] Notice: The portion of the term of this patent subsequent to Jun. 4, 2002 has been disclaimed.

[21] Appl. No.: 570,343

[22] Filed: Jan. 13, 1984

[51] Int. Cl.[4] .............................................. A61F 5/02
[52] U.S. Cl. ................................ 128/78; 128/87 R; 128/90; 128/68
[58] Field of Search ..................... 128/78, 90, 69, 68, 128/75, 87 R, 87 B

[56] References Cited

U.S. PATENT DOCUMENTS

| Re. 31,564 | 4/1984 | Hendricks | 128/78 |
|---|---|---|---|
| 2,796,866 | 6/1957 | Cohen | 128/78 |
| 3,620,211 | 11/1971 | Goodell et al. | 128/78 X |
| 3,662,057 | 5/1972 | Webster et al. | 128/90 X |
| 3,667,457 | 6/1972 | Zumaglini | 128/75 |
| 3,771,513 | 11/1973 | Velazquez | 128/87 B |
| 3,878,840 | 4/1975 | Esbelin | 128/70 |
| 3,945,376 | 3/1976 | Kuehnegger | 128/78 |
| 4,024,861 | 5/1977 | Vincent | 128/87 R |
| 4,034,748 | 7/1977 | Winner | 128/87 R |
| 4,194,501 | 3/1980 | Watt | 128/75 |
| 4,204,529 | 5/1980 | Cochrane | 128/75 |
| 4,383,523 | 5/1983 | Schurman | 128/75 |
| 4,520,801 | 6/1985 | Lerman | 128/87 B X |

Primary Examiner—Richard J. Apley
Assistant Examiner—Alan W. Cannon
Attorney, Agent, or Firm—Christie, Parker & Hale

[57] ABSTRACT

A cervical thoracic orthosis includes a chest plate and a back plate for overlying a patient's chest and back, fastening means for securing in a fixed position around the patient's upper torso, an occipital support shaped to conform to the occipital region of the patient's head, an occipital support bar secured to the occipital support and fastened to the back plate a chin support shaped to conform to the chin and lower jaw region of the patient, and a chin support bar secured to the chin support and fastened to the chest plate. In one embodiment, the chin support is hinged to the chin support bar so the chin support can rotate to a desired angle at which the patient's head is held. Adjustable fasteners extending between the occipital support and the chin support are secured to hold the patient's head in the desired angular position. The occipital support bar extends vertically and is shaped to provide a rigid means of support conforming to the shape of the patient's upper cervical spine. The occipital support also includes a U-shaped lateral support bar extending around the occipital region of the patient's head to reinforce the occipital support and prevent rotation of the patient's head. The chest plate, back plate, occipital support and chin support are all made from a thin, semi-rigid shell lined with an inner layer of an open cell containing resilient foam. The shells bend to conform to anatomical contours.

12 Claims, 7 Drawing Figures

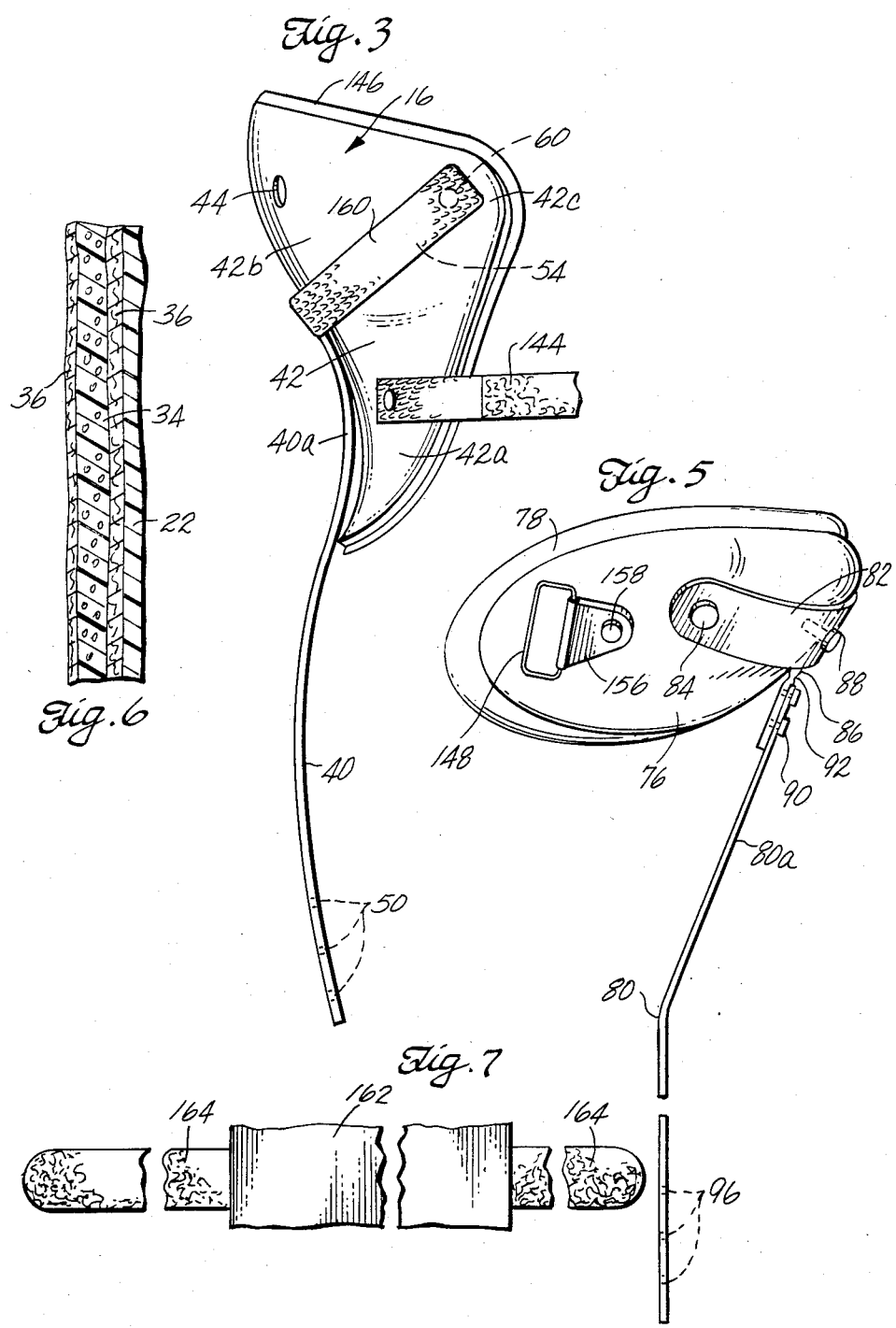

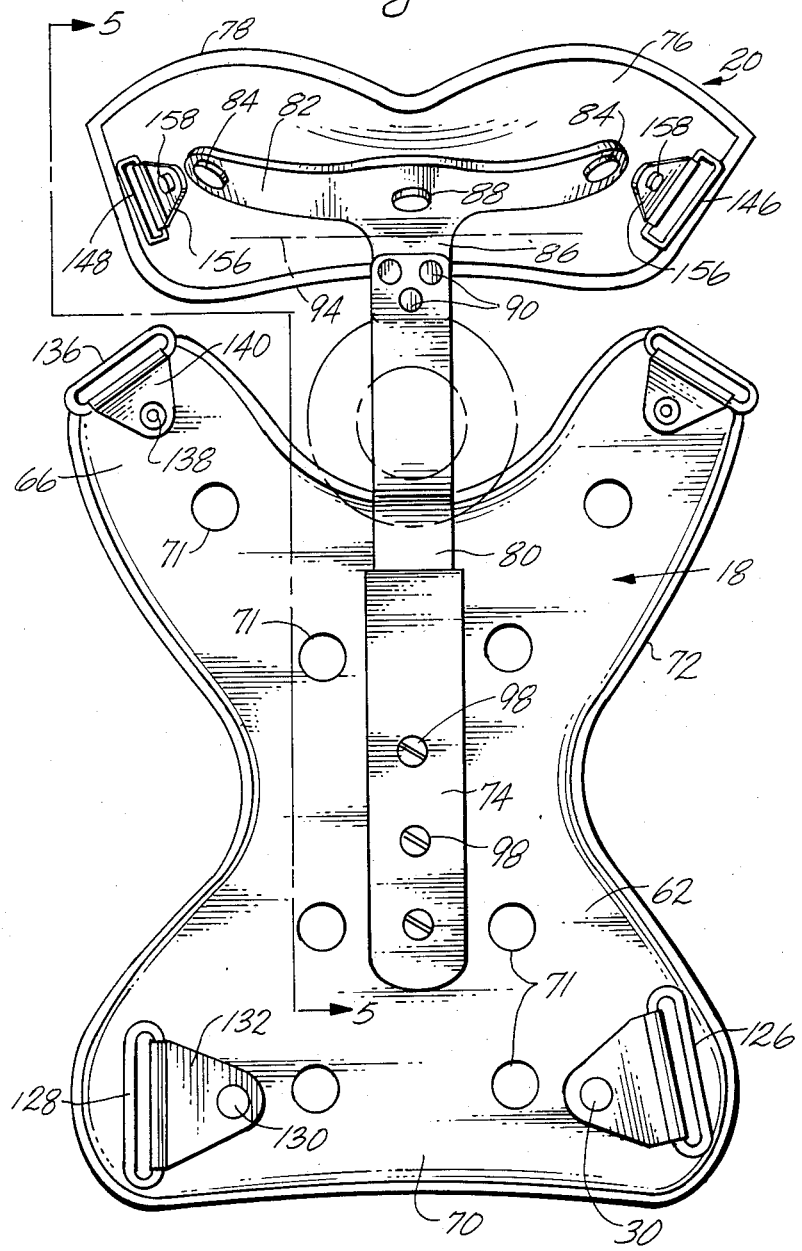

CERVICAL THORACIC ORTHOSIS

BACKGROUND OF THE INVENTION

This invention relates to a cervical thoracic orthosis for use in immobilizing the head and neck region of a patient, particularly one who has had an upper spinal cord fracture.

A cervical injury, such as a fracture to the upper cervical spine, requires immobilization of the head, neck and sternum so that the upper cervical spine is not moved. There is a need for an orthosis that immobilizes the head and neck of the patient, particularly when the patient is lying in a hospital bed. There is also a need to ensure that adjustments can be made to immobilize the patient's head in a desired position. A hospital patient having a fracture of the upper cervical spine can require immobilization over a long period of time. Thus, an orthosis for immobilizing the upper cervical spine should remain reasonably comfortable when worn by a hospital patient for a long period of time. In the past, braces used for immobilizing spinal fractures have not been particularly comfortable for the patient who lies on his back for long periods of time. Other braces have not provided effective means of preventing rotation of the head or providing adjustments to the position in which the head is immobilized. Further, other braces have used padding of a closed cell polymeric foam material. This material can make the brace appear to be reasonably comfortable because of the cushioning it provides. However, the brace is not comfortable when worn continuously over long periods of time. A closed cell material does not "breathe", and when the brace is worn for a long time, it can cause the patient to perspire which can lead to heat rashes and other discomforting skin problems. Closed cell foam materials do not breathe in the sense that they are resistant to air circulation through them, and they do not absorb fluids.

The present invention provides a cervical thoracic orthosis which is of low profile and easily bendable to conform to the shape of the anatomical regions of the patient's body supported by the orthosis. The orthosis thus can be comfortably worn over long periods of time by a hospital patient whose upper cervical spine is being immobilized. The cervical thoracic orthosis of this invention is made, in part, from an open cell foam material which breathes during use, and therefore does not create skin problems or other discomfort when the orthosis is worn for a long time. Open cell materials are not capable of being molded to the desired anatomical shape as are closed cell materials. However, the cervical thoracic orthosis of this invention is made so that the open cell material is supported in the desired anatomical shape to provide the comfort not provided by a closed cell material; and yet the orthosis of this invention provides the desired comfort while also providing the required stability of support for the patient wearing it. The orthosis can securely maintain the patient's upper cervical spine completely immobilized, preventing undesired rotation of the patient's head, while also securely yet comfortably maintaining the patient's head in a desired angular position during immobilization.

SUMMARY OF THE INVENTION

Briefly, the cervical thoracic orthosis includes a chest plate for overlying the chest region of a patient and a back plate for overlying the back of the patient. The chest plate and back plate are secured in a fixed position around the front and back sides of the patient's upper torso. A chin support secured to the chest plate holds the chin of the patient in a fixed position. An occipital support secured to the back plate holds the occipital portion of the patient's head in a fixed position. In one embodiment, the chin support is hinged to adjust the angle at which the chin is supported. The chin support is secured in a fixed position to hold it at the adjusted angle. In one form of the invention, the chin support includes a chin-supporting pad hinged to a rigid bar which in turn is affixed to the chest plate. The hinge allows the chin-supporting pad to rotate about a substantially horizontal axis to change the angle between the chin-supporting pad and the bar. Fastening means extend around both sides of the patient's head for attaching the chin-supporting pad to the occipital support to hold the hinged chin-supporting pad at the desired angular adjustment.

In another embodiment, the occipital support includes a rigid support bar affixed to an occipital support pad that fits under the occiptal region of the patient's head. The bar is affixed to the back plate to hold the occipital support pad in place. The upright bar extends up along the upper cervical spine of the patient to the occipital region of the patient's head. This bar conforms to the contour of the patient's upper cervical spine and provides rigid support for it. A generally U-shaped rigid bar secured to the occipital support pad extends around opposite sides of the occipital region of the patient's head. The U-shaped bar provides stiffness for the occipital support to resist rotation of the patient's head.

The chin support and the occipital support each are preferably made from a preformed, semi-rigid, one-piece shell in a three-dimensional anatomical shape that conforms to the underside of the chin region and the occipital region of the patient's head. Each shell is bendable to conform to the anatomical shape of the patient's head. The inside face of each shell has a resilient open cell layer on the side for contact with those anatomical regions to which the shape of the shell conforms. The semi-rigid preformed shell facilitates use of the open cell material for padding which makes the chin support and occipital support comfortable for the patient during long periods of use. Skin rashes and other problems created by prolonged use of the chin and occipital support made from a closed cell material, for example, are alleviated. The chin-supporting and occipital-supporting shells are each reinforced by their supporting bars and this adds stiffness to each shell so that the shell has sufficient rigidity to support the patient and immobilize the upper cervical spine, while the open cell-containing padding and the semi-rigid shell provide comfort during long periods of use.

These and other aspects of the invention will be more fully understood by referring to the following detailed description and the accompanying drawings.

DRAWINGS

FIG. 3 is a fragmentary side elevation taken on line 3—3 of FIG. 2.

FIG. 4 is a front elevation view showing a chest plate and chin support.

FIG. 5 is a side elevation view of the chin support taken on line 5—5 of FIG. 4.

FIG. 6 is a fragmentary cross-sectional view taken on line 6—6 of FIG. 2.

FIG. 7 is a fragmentary front elevation showing fastening means for holding a patient's head in a fixed position.

DETAILED DESCRIPTION

Figure 1:
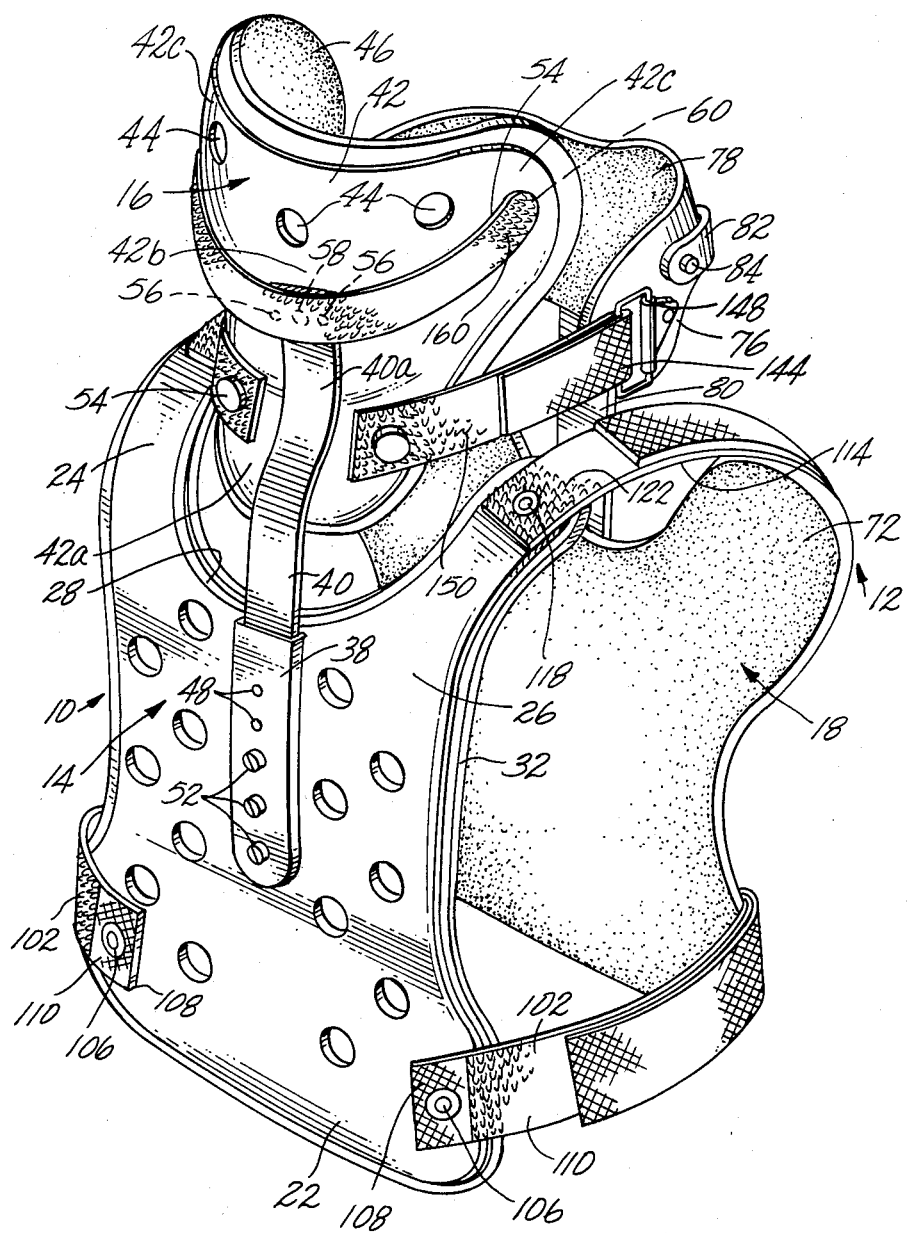
FIG. 1 is a perspective view showing front and rear portions of a cervical thoracic orthosis according to principles of this invention.

FIG. 1 is a perspective view showing a cervical thoracic orthosis according to principles of this invention. The orthosis includes a rear piece 10 and front piece 12 which are secured around the patient and to each other for holding the patient's head, neck and upper torso in a fixed position to immobilze the patient's upper cervical spine. The rear piece 10 includes a back plate 14 for overlying the upper region of the patient's back. The back plate holds an occipital support 16 under the occipital region of the patient's head. The front piece 12 includes a chest plate 18 for overlying the patient's sternum. The chest plate holds a chin support 20 under the patient's chin.

Figure 2:
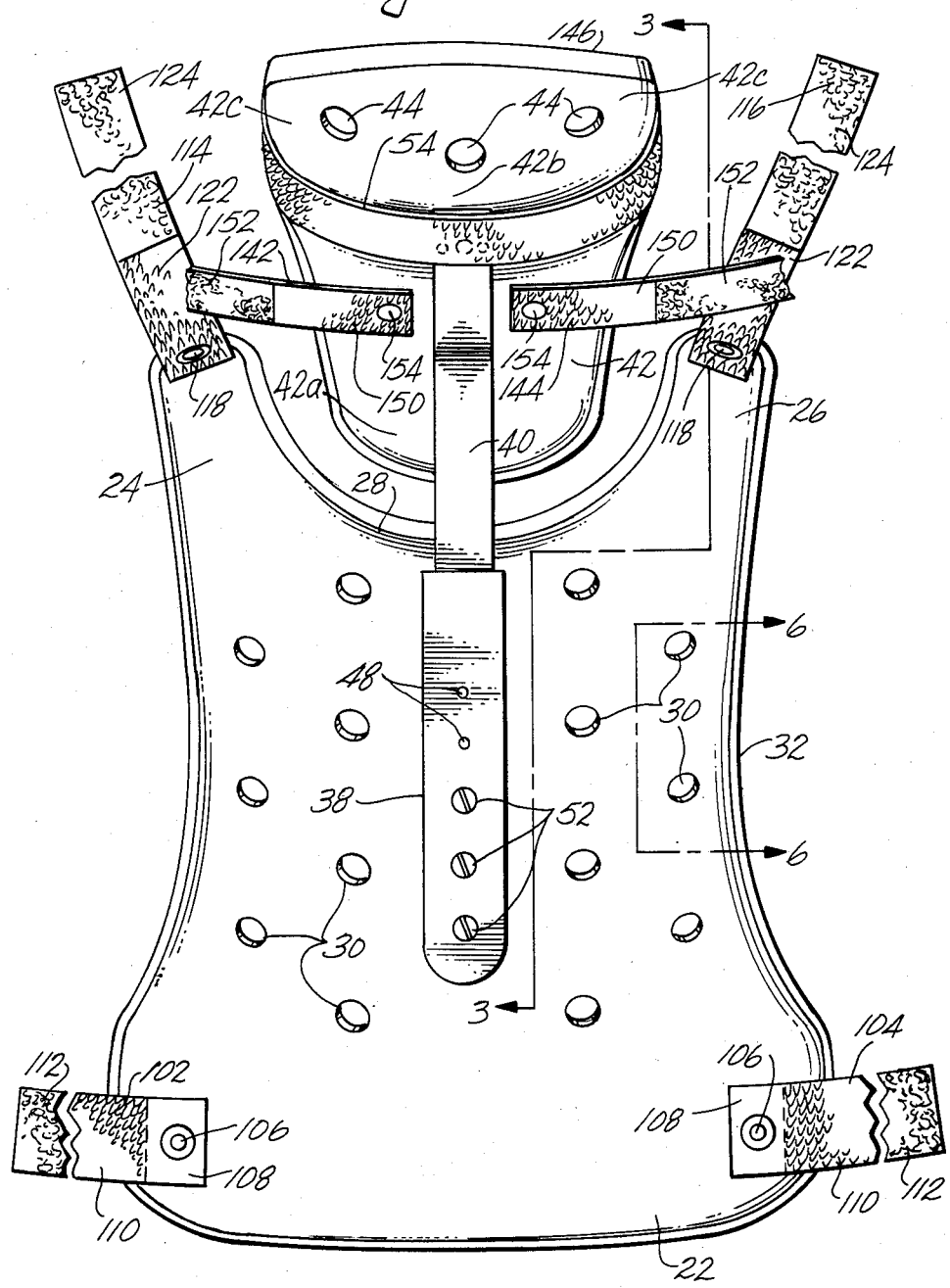
FIG. 2 is a fragmentary front elevation view showing a back plate and occipital support.

Construction of the back plate 14 and occipital support 16 are understood best by referring to FIGS. 2 and 3 in conjunction with FIG. 1. The back plate includes a semi-rigid, self-supporting shell 22 made of a material preformed to an anatomical shape to overlie the upper portion of the patient's back. The width of the shell extends across the width of the patient's back. The length of the shell extends from about the small of the patient's back upwardly to a pair of left and right upper extensions 24 and 26 that overlie left and right rear portions of the patient's shoulder blades. The upper central portion of the shell has a U-shaped recess 28 that extends below the patient's upper cervical spine. The shell 22 is preferably made from a thin sheet of polyethylene that is sufficiently flexible to be vacuum formed into the desired shape and which remains reasonably flexible after shaping. Air holes 30 are left in the shell to improve air circulation during use.

A layer 32 of padding covers the inside face of the shell 22. The layer preferably comprises an internal layer 34 (see FIG. 6) of an open cell resilient plastic foam material such as polyurethane foam. The open cell foam material is used because it is capable of "breathing", i.e., it allows circulation through the cells and absorbs moisture, as opposed to a closed cell material which does not breathe appreciably and which does not absorb fluids to any significant extent. The open cell foam layer is enclosed within an outer layer 36 of a soft flexible fabric that is also capable of breathing and is comfortable when in direct contact with the skin for long periods of time. A preferred outer layer material is velour. The enclosure formed by the velour is preferably made by overlaying two pieces of velour on opposite faces of the open cell foam layer and then fastening the overlying layers of velour by stitching around the entire outer perimeter of the foam layer. The resulting padding is then affixed to the inside face of the shell by a suitable adhesive. The padding covers the entire inside face of the shell including the upper left and right extensions 24 and 26.

A narrow elongated upwardly opening receptacle 38 is formed along the center of the back plate. The receptacle is integrally formed with the wall of the shell 22. The receptacle is formed during the vacuum-forming process by placing a long, narrow, flat insert in the mold and forming the outer wall of the receptacle from the same material as the wall of the shell. The insert is then removed, leaving the receptacle as a long narrow projection of a low profile with an opening at its top. The inner layer of padding 32 forms the inside face of the receptacle.

The receptacle receives the lower end of a rigid occipital support bar 40 of the occiptal support 16. The bar supports an occipital support pad which includes a thin, semi-rigid shell 42 preformed to the anatomical shape of the rear portion of the patient's head and the rear of the patient's neck. A lower portion 42a of the shell overlies the rear portion of the patient's neck, and the shell tapers wider upwardly and extends outwardly to form a cup-shaped upper region 42b for overlying and conforming to the contour of the occipital region of the patient's head. The upper portion of the occipital support shell 42 flares outwardly to form left and right upper sections 42c that extend around the left and right rear sides of the patient's head generally above the occipital region of the head. Air holes 44 are left in the shell that forms the occipital support. The shell is made from the same type of thin sheet vaccum-formable material such as polyethylene from which the shell 22 of the back plate is made. In addition, the inside face of the occipital support pad has a layer of open cell foam padding 46 similar to the padding 32 on the inside face of the shell 22.

A series of vertically spaced apart holes 48 are formed in the outer wall of the receptacle 38 on the back plate 14. A corresponding set of holes 50 (see FIG. 3) with the same spacing extend through the lower portion of the bar 40. The bar is made from a metal such as aluminum. The lower portion of the bar is rigid, but the upper portion is annealed to make the bar more bendable than the lower portion of the bar. The bar is inserted into the receptacle and moved to the proper height adjustment for the occipital support 16. The holes 50 in the bar are threaded internally, and the bar 40 is held in a fixed position by aligning the holes in the bar with corresponding holes in the receptacle, after which fasteners 52 are inserted into the holes in the receptacle and threaded into the holes in the bar for holding the occipital support in place. As shown best in FIG. 3, the upper portion of the bar 40 is bent inwardly at 40a to conform to the contour of the patient's neck. The bar is then bent outwardly near its top to conform to the shape of the occiptal region of the patient's head. The upper end of the bar terminates in the vicinity of the occipital region. The upper portion of the bar 40 which extends above the recess 28 in the back plate conforms closely to the contour of the upper cervical spine to provide a rigid means of support along the upper cervical spine. The lower portion of the bar provides a rigid means of support along the patient's spinal column below the patient's neck.

A generally U-shaped elongated metal lateral support bar 54 of narrow profile extends generally horizontally from left to right across the cup-shaped region 42b of the occipital supporting shell 42. The lateral bar 54 is rigidly affixed at its center to the upper end of the occipital support bar 40 by fasteners 56. A rivet 58 extends through the center of the lateral bar 54 and the upper end of the occipital support bar 40 and through the shell 42a for rigidly fastening both bars to the center rear portion of the shell. Rivets 60 at opposite ends of the lateral support bar 54 extend through the bar and through the shell for affixing the ends of the bar to the upper outer sections 42c of the shell. The lateral support bar 54, in use, provides a means of rigid support across the occipital region of the patient's head extending from the vicinity behind one ear across the occipital region to the vicinity behind the ear on the opposite side of the patient's head.

The chest plate 18 comprises a thin, semi-rigid shell 62 in a three-dimensional anatomical shape to overlie the patient's sternum. The chest plate has upward and outwardly projecting left and right upper portions 64 and 66 (left and right as viewed when worn) for overlying left and right portions of the patient's clavicle. The upper edge of the shell has a central U-shaped recess 68 for extending below the patient's neck. The opposite outer edges of the shell taper downwardly inwardly toward the middle of the shell and then diverge downwardly and outwardly toward an enlarged lower portion 70 of the shell that overlies the patient's midriff. The chest plate is preferably made from thin-walled three-dimensionally formed flexible plastic material such as polyethylene. Spaced apart air holes 71 are left in the shell to enhance air circulation. The inside face of the shell is preferably covered by a layer 72 of an open cell material with an outer layer of velour as used on the inside of the back plate.

A long, narrow upright receptacle 74 extends along the center of the chest plate. The receptacle has an opening at its top and is of narrow profile, made by the same technique as the receptacle 38 on the back plate. The chin support 20 includes a chin-supporting pad made from a thin-walled, semi-rigid shell 76 preformed to conform to the anatomical shape of the patient's chin and opposite sides of the patient's lower jaw. The shell is an upwardly opening generally cup-shaped piece formed into the three-dimensional shape from a thin-walled flexible but self-supporting plastic material such as polyethylene. A layer 78 of an open cell foam material similar to the padding 46 on the occipital support overlies the inside face of the shell 76. An upright rigid metal bar 80 extends vertically below the chin support. A semi-rigid lateral support 82 overlies the front face of the shell 76 and extends under the chin region of the shell. The outer ends of the lateral support are affixed to the shell by rivets 84. As shown best in FIG. 5, the support 82 hinges the chin support pad to the upper end of the chin support bar 80. A hinge is formed from a short piece 86 of the support which extends down below the lateral extension of the support. A rivet 88 rigidly secures an upper portion of the hinge to the center of the chin support. The lower portion of the hinge is rigidly affixed to the upper end of the chin support bar by rivets 90. A living hinge 92 extends across the width of the hinge between the top of the bar and the bottom edge of the lateral bar. This provides a horizontal axis 94 about which the chin support pad can rotate.

An upper portion 80a of the chin support bar is annealed so that portion of the bar is more easily bendable than the rigid lower portion of the bar which fits into the long narrow opening inside the receptacle 74 in the front of the chest plate. Spaced apart threaded holes 96 in the lower portion of the bar are aligned with holes in the receptacle when adjusting the chin support pad upwardly or downwardly to the desired elevation. Fasteners 98 are threaded into the holes in the bar 80 for securing the bar in a fixed position on the chest plate. The upper portion of the bar is bent inwardly to match generally the contour of the front of the patient's neck. The lateral support 82 is made of plastic but adds rigidity to the chin support pad to assist in immobilizing the patient's chin, while the flexibility of the shell and the open cell padding maintain long term comfort of the chin support.

FIG. 4 schematically illustrates an alternative form of the chin support in which the chin support bar can be ring-shaped with a central opening 100 to provide access for tracheotomy patients.

In using the cervical thoracic orthosis, the occipital support bar 40 is placed in the receptacle 38 in the back plate, but not fastened to the receptacle, so that the bar is slidable up or down in the receptacle. The back plate is then placed under the back of the patient with the right and left upper extensions of the back plate overlying the right and left rear portions of the patient's shoulder blades. The patient's head is held in the desired angular position, for instance, either in extension (chin up) or in flexion (chin down). The occiptal support bar is slid vertically in the receptacle to place the occipital support 16 under the occipital region of the patient's head. The chest plate is then placed over the patient's sternum with the left and right upper portions 64, 66 of the chest plate extending to the vicinity of the patient's clavicle. The back plate and the chest plate are then fastened to each other firmly around the patient's upper torso. In the illustrated embodiment, the back plate has left and right lower flexible straps 102 and 104 extending away from the left and right lower sides of the back plate. Each lower strap is secured to the shell 22 by rivets 106 which extends through a vinyl reinforced end portion 108 of the strap. The attachments by the rivets 106 allow each strap to rotate through an angle relative to the shell. The portions of the straps closest to the back plate have a length of a first type of thistle cloth fastener 110, preferably a length of Velcro-type hook material fastened to the outer face of the strap by stitching. The fastener sections 110 extend for about one-third the length of the lower straps, and the remaining length of each lower strap has a long section of a second type of thistle cloth material 112, preferably a Velcro-type pile material. The back plate also has a pair of left and right upper straps 114 and 116 fastened to the left and right upper extensions 24 and 26 of the back plate shell 22. The upper straps are affixed to the back plate in a manner similar to the lower straps in that each strap is fastened to the shell by a rivet 118 extending through a vinyl reinforced section 120 at the end of the shell. A short length of the outer face of each strap has a Velcro-type hook material 122, and the longer end portion of each upper strap has a length of a Velcro-type pile material. The upper and lower straps are each preferably made of a durable flexible material such as nylon.

A pair of left and right lower fastener rings 126 and 128 are fastened to the left and right sides of the lower portion 70 of the chest plate. Each of the lower fastener rings is preferably fastened to the shell by a rivet 130 extending through a vinyl ring holder 132. The rivets allow each fastener ring to pivot relative to the shell. Similarly, left and right upper fastener rings 134 and 136 are fastened to the left and right upper extensions 64 and 66 of the chest plate. Each of the fastener rings is affixed to the shell by a rivet 138 and a ring holder 140. These fastener rings are also able to rotate relative to the chest plate.

The back plate and chest plate are firmly affixed around the patient's torso by fastening the left and right lower straps 102 and 104 to the left and right fastener rings 126 and 128 and by fastening the left and right upper straps 114 and 116 to the left and right fastener rings 134 and 136 on the chest plate. Each strap is threaded through its corresponding fastener ring, and then pulled tightly and folded back on itself to fasten the Velcro-type pile material on the fastener to the adjacent Velcro-type hook material on the same strap. This allows the back plate and chest plate to be firmly affixed around the patient's rib cage. The occipital support and the chin support are then placed in their required positions for immobilizing the patient's head, after which the occipital support and the chin support are fastened to the back plate and the chest plate. By holding the patient's head in the desired angular position, the chin support pad is able to rotate about the axis 94 through the hinge 86 so that the chin support can be moved to the correct angular orientation for holding the patient's chin at the desired angle. Once the chin support and occipital support are positioned in their desired positions, the chin support is affixed in place by tightening the fasteners 98, and the occipital support is then locked in place by tightening the fasteners 52.

The occipital support has a pair of left and right flexible straps 142 and 144 which extend around the left and right sides of the patient's head for attachment to left and right fastener rings 146 and 148 affixed to left and right sides of the chin support shell 76. The left and right straps on the occipital support include a first section of a Velcro-type hook material 150 and a longer outer section 152 of a Velcro-type pile material. Each of these straps is affixed to the occipital support shell 42 by a fastener 154. Each of the fastener rings 146 and 148 on the chin support is secured to the shell of the chin support by a flexible ring holder 156 and a fastener 158. The occipital support straps are threaded through the fastener rings on the chin support and then folded back on themselves to pull the occipital support and the chin support in its desired angular orientation tightly around the patient's head. The occipital support shell and the chin support shell are able to bend to conform to the contour of the patient's head. The cooperating Velcro fasteners are then attached to each other to hold the chin support in the desired angular orientation relative to the occipital support. As an additional means of holding the patient's head in the desired position, an elongated length of a Velcro hook fastener 160 is affixed to the outer face of the lateral support bar 54 on the occipital support. Referring to FIG. 7, a forehead support pad 162 is then placed against the patient's forehead, and straps 164 extending outwardly from the support pad are extended around opposite sides of the patient's head to the Velcro fastener 160 on the occipital support. The straps 164 have a Velcro-type pile material for attachment to the Velcro-type hook material of the fastener 160. This provides an additional means for holding the patient's head in the desired angular position.

The cervical thoracic orthosis is comfortable for a hospital patient who wears the orthosis over a long period of time. Comfort is enhanced because the orthosis is of low profile and is made from a flexible material that is bendable to conform well to the anatomical shape of the patient's head, neck and upper torso. The orthosis is comfortable, in addition, because of the open cell containing material that provides the padding for all support areas of the orthosis. In addition to being comfortable, the orthosis provides rigid means of support in positions that ensure immobilization of the patient's head, neck and chest areas. The orthosis also resists rotation of the patient's head and ensures immobilizing the patient's head in the desired angular position. The orthosis thus prevents the upper cervical spine from being moved.

I claim:

1. A cervical thoracic orthosis comprising:
a chest plate for overlying a patient's chest;
a back plate for overlying a patient's back;
an occipital support for supporting the occipital and neck region of the patient;
a rigid occipital support bar secured to the occipital support;
means for fastening the occipital support bar to the back plate for holding the occipital support in a fixed position against the occipital and neck region of the patient;
a chin support for supporting the chin and lower jaw region of the patient's head;
a rigid chin support bar secured to the chin support;
means for fastening the chin support bar to the chest plate for holding the chin support in a fixed position against the chin and lower jaw region of the patient's head; and
means for fastening the chest plate and the back plate in a fixed position around the patient's upper torso for holding the occipital support and the chin support in their fixed positions;
the occipital support bar having a lower portion for providing a rigid means of support extending along the center of the patient's back to support the spinal column below the patient's neck,
the occipital support bar having an upper portion for extending along the upper cervical spine of the patient, said upper portion of the occipital support bar curving inwardly to conform to and provide a rigid means of support extending along the neck region of the patient, the top of the occipital support bar curving outwardly to conform to and provide a rigid means of support for the occipital region of the patient's head,
the occipital support having an upper portion shaped to conform to the occipital region of the patient's head and a lower portion extending downwardly therefrom and curved inwardly relative to said upper portion to conform to the back of the patient's neck region,
the upper portion of the occipital support bar being secured to the upper and lower portions of the occipital support to provide rigid support for portions of the occipital support in contact with the upper cervical spine of the patient along the neck and occipital regions of the patient.

2. Apparatus according to claim 1 including a rigid lateral support bar on the occipital support extending generally perpendicular to the occipital support bar and curved along its opposite sides for providing a rigid means of support conforming generally to the sides of the occipital region of the patient's head; and in which the occipital support is a semi-rigid bendable material for conforming to the shape of the patient's neck and occipital regions.

3. Apparatus according to claim 1 including an elongated narrow and rigid receptacle extending along the rear center of the back plate and conforming closely to the width of the lower portion of the occipital support bar to provide a guide within which the lower portion of the occipital support bar slides relative to the back plate; and fastening means for maintaining the lower portion of the occipital support bar in a fixed position in the narrow elongated receptacle, to provide a means for guiding travel of the lower portion of the occipital support bar along the back plate and for fastening the bar relative to the receptacle.

4. Apparatus according to claim 1 in which the chin support and the occipital support are both made of semi-rigid bendable materials; and including flexible straps extending between the occipital support and the chin support along both sides of the patient's head for fastening the occipital support and the chin support in a fixed position around the patient's head.

5. Apparatus according to claim 1 including hinge means for securing the chin support to the chin support bar to allow the chin support to pivot about a generally horizontal axis for holding the chin at a desired angle of inclination; and means for fastening the occipital support and the chin support in a fixed position around the patient's head for holding the chin support at the desired angle.

6. Apparatus according to claim 1 including additional fastening means for extending around the upper portions of the patient's head and for attachment to the occipital support for additionally immobilizing the patient's head against rotation.

7. A cervical thoracic orthosis comprising:
a chest plate for overlying a patient's chest;
a back plate for overlying a patient's back;
an occipital support for supporting the occipital and neck region of the patient;
a rigid occipital support bar secured to the occipital support;
means for fastening the occipital support bar to the back plate for holding the occipital support in a fixed position against the occipital and neck region of the patient;
a chin support for supporting the chin and lower jaw region of the patient's head;
a rigid chin support bar secured to the chin support;
means for fastening the chin support bar to the chest plate for holding the chin support in a fixed position against the chin and lower jaw region of the patient's head;
means for fastening the chest plate and the back plate in a fixed position around the patient's upper torso to hold the occipital support and the chin support in their fixed positions;
means for fastening the chin support to the occipital support along opposite sides of the patient's head;
the occipital support bar having a lower portion for providing a rigid means fo support extending along the center of the patient's back to support the spinal column below the patient's neck;
the occipital support bar having an upper portion for extending along the upper cervical spine of the patient, said upper portion of the occipital support bar curving inwardly to conform to and provide a rigid means of support extending along the neck region of the patient, the top of the occipital support bar curving outwardly to conform to and provide a rigid means of support for the occipital region of the patient's head,
the occipital support having an upper portion shaped to conform to the occipital region of the patient's head and a lower portion extending downwardly therefrom and curved inwardly relative to said upper portion to conform to the back of the patient's neck region;
the upper portion of the occipital support bar being secured to the upper and lower portions of the occipital support to provide rigid support for portions of the occipital support in contact with the upper cervical spine of the patient along the neck and occipital regions of the patient;
the chest plate, back plate, occipital support and chin support each being made from a thin-walled semi-rigid bendable self-supporting material preformed in a three-dimensional shape to match the contour of the anatomical regions they support, and a layer of open cell-containing material on the inside face of the chest plate, the back plate, the occipital support and the chin support; the layers of open cell material thereby being held in close contact with the corresponding anatomical regions of the patient as the fastening means are tightened to bend the chest plate, back plate, occipital support and chin support into close contact with the corresponding anatomical regions of the patient.

8. Apparatus according to claim 7 including a rigid lateral support bar on the occipital support extending generally perpendicular to the occipital support bar and curved along its opposite sides for providing a rigid means of support conforming generally to the sides of the occipital region of the patient's head.

9. Apparatus according to claim 7 including an elongated narrow and rigid receptacle extending along the rear center of the back plate and conforming closely to the width of the lower portion of the occipital support bar to provide a guide within which the lower portion of the occipital support bar slides relative to the back plate; and fastening means for maintaining the lower portion of the occipital support bar in a fixed position in the narrow elongated receptacle, to provide a means for guiding travel of the lower portion of the occipital support bar along the back plate and for fastening the bar relative to the receptacle.

10. Apparatus according to claim 7 including flexible straps extending between the occipital support and the chin support along both sides of the patient's head for fastening the occipital support to the chin support.

11. Apparatus according to claim 7 including hinge means for securing the chin support to the chin support bar to allow the chin support to pivot about a generally horizontal axis for holding the chin at a desired angle of inclination; and means for fastening the occipital support and the chin support in a fixed position around the patient's head for holding the chin support at the desired angle.

12. Apparatus according to claim 7 including additional fastening means for extending around the upper portions of the patient's head and for attachment to the occipital support for additionally immobilizing the patient's head against rotation.

* * * * *